(12) United States Patent
Krijnsen et al.

(10) Patent No.: US 9,386,925 B2
(45) Date of Patent: Jul. 12, 2016

(54) DEVICE FOR DRUG ADMINISTRATION AND/OR MONITORING THE STATUS OF A PATIENT

(75) Inventors: Henrike Krijnsen, Boxtel (NL); Geert Langereis, Eindhoven (NL); Michel Van Bruggen, Helmond (NL); Ventzeslav Iordanov, Valkenswaard (NL)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 1767 days.

(21) Appl. No.: 12/299,809

(22) PCT Filed: May 2, 2007

(86) PCT No.: PCT/IB2007/051633
§ 371 (c)(1),
(2), (4) Date: Nov. 6, 2008

(87) PCT Pub. No.: WO2007/132379
PCT Pub. Date: Nov. 22, 2007

(65) Prior Publication Data
US 2009/0099508 A1    Apr. 16, 2009

(30) Foreign Application Priority Data
May 11, 2006    (EP) .................................. 06113786

(51) Int. Cl.
*A61B 5/024* (2006.01)
*A61B 5/01* (2006.01)
*A61M 5/168* (2006.01)
*A61B 5/0205* (2006.01)
*G06F 19/00* (2011.01)
*A61B 5/00* (2006.01)
*A61B 5/02* (2006.01)

(52) U.S. Cl.
CPC ................. *A61B 5/0205* (2013.01); *A61B 5/00* (2013.01); *A61B 5/02055* (2013.01); *G06F 19/3468* (2013.01); *A61B 5/01* (2013.01); *A61B 5/02* (2013.01); *A61B 5/024* (2013.01)

(58) Field of Classification Search
CPC   A61B 5/0205; A61B 5/02055; G06F 19/345; G06F 19/3481; G06F 19/3406; G06F 19/3468; G06F 19/3456; G06F 19/3475
USPC .............................. 604/890.1; 600/485, 500
See application file for complete search history.

(56) References Cited

U.S. PATENT DOCUMENTS

| | | | | |
|---|---|---|---|---|
| 4,003,379 | A | * | 1/1977 | Ellinwood, Jr. ............ 604/891.1 |
| 4,216,779 | A | * | 8/1980 | Squires ................ A61B 5/7285 128/900 |
| 4,756,706 | A | * | 7/1988 | Kerns ................... A61M 5/1413 128/DIG. 13 |
| 5,300,092 | A | | 4/1994 | Schaldach |
| 5,730,137 | A | * | 3/1998 | Amano et al. ................. 600/485 |

(Continued)

FOREIGN PATENT DOCUMENTS

| EP | 0721764 A2 | 7/1996 |
|---|---|---|
| JP | 05015595 A | 1/1993 |
| WO | 03079894 A1 | 10/2003 |

*Primary Examiner* — Nathan R Price
*Assistant Examiner* — William Carpenter
(74) *Attorney, Agent, or Firm* — Lee & Hayes, PLLC

(57) ABSTRACT

The invention relates to a device for drug administration and/or monitoring the status of a patient, the device comprising a first and a second measuring means, and the time for using the second measuring means being set in accordance with the data of the first measuring means.

8 Claims, 2 Drawing Sheets

(56) References Cited

U.S. PATENT DOCUMENTS

| | | | |
|---|---|---|---|
| 5,743,268 A * | 4/1998 | Kabal | A61B 5/02028 600/485 |
| 5,743,857 A | 4/1998 | Shinoda et al. | |
| 5,810,737 A | 9/1998 | Dardik | |
| 6,027,455 A * | 2/2000 | Inukai | A61B 5/02125 600/485 |
| 6,334,065 B1 * | 12/2001 | Al-Ali et al. | 600/323 |
| 6,743,179 B2 * | 6/2004 | Narimatsu et al. | 600/485 |
| 6,929,636 B1 * | 8/2005 | von Alten | 604/890.1 |
| 7,594,893 B2 * | 9/2009 | Tao et al. | 600/500 |
| 2003/0208154 A1 | 11/2003 | Close et al. | |
| 2005/0058701 A1 * | 3/2005 | Gross | G01K 13/002 424/451 |
| 2006/0052711 A1 * | 3/2006 | Chang | A61B 5/0205 600/485 |
| 2006/0281983 A1 * | 12/2006 | Al-Ali et al. | 600/323 |
| 2008/0262478 A1 * | 10/2008 | Krijnsen | A61B 5/00 604/890.1 |
| 2008/0294096 A1 * | 11/2008 | Uber et al. | 604/66 |
| 2009/0054908 A1 * | 2/2009 | Zand et al. | 606/130 |
| 2010/0063367 A1 * | 3/2010 | Friedman et al. | 600/301 |

* cited by examiner

DEVICE FOR DRUG ADMINISTRATION AND/OR MONITORING THE STATUS OF A PATIENT

This invention is in the field of devices for the analysis of a patient as well as devices for drug administration, especially for hypertension treatment.

The concept of homeostasis stipulates that there is constancy of the endogenous compounds in blood. This is a most powerful construct in biology, and has influenced not only the teaching and understanding of the medical sciences but also the practice of clinical medicine. According to this concept, the risk of the occurrence and exacerbation of disease is independent of the time of day, day of month, and month of year, as is the response of patients to diagnostic tests and medications. However, most biological functions and processes are anything but constant; findings from the field of biologic rhythm study (chronobiology) challenge the concept of homeostasis, as well as many of the assumptions and procedures of clinical medicine.

Many biological functions wax and wane in cycles that repeat on a daily, monthly or annual basis. Such patterns do not reflect simply an organism's passive response to environmental changes, such as daily cycles of light and darkness. Rather, they reflect the organism's biological rhythms, that is, its ability to keep track of time and to direct changes in function accordingly.

Especially in the field of hypertension it has been found that the chronobiological aspect may play an important role when analyzing hypertension and applying the correct drug treatment.

Due to neurohormonal changes, the typical circadian variation in blood pressure for the majority of hypertensive patients follows a nadir occurring during the nighttime hours and a surge during the early morning period.

It is therefore an object of the present invention to provide a device for the analysis and/or drug administration for hypertension which is adapted to take into account the circadian rhythm of a patient.

This object is achieved by a device according to claim 1 of the present invention. Accordingly, a device for drug administration is provided, comprising
a) a measuring means, which measures at least one first body parameter of a patient for at least 1 measuring cycle and at least 1 monitoring cycle,
b) a normalizing means, which generates a normalized curve for each of the measured body parameters of the patient from the data obtained in the measuring cycles and adjusts the data obtained in the at least one monitoring cycle to normalized data based on the normalized curve to obtain normalized monitoring data,
c) a second measuring means which measures at least one second body parameter in response to the output of the normalizing means of the at least one first body parameter,
d) optionally, a comparison means which compares the second body parameter data with pre-stored comparison data,
e) optionally, a drug delivery device which comprises a drug release means, which starts a drug release program based upon the comparison between the second body parameter data and the pre-stored comparison data.

As a result, at least one of the following advantages is achieved for most of the applications within the present invention:

Due to the presence of two measuring means, of which the second measuring means measures data based (?) upon the data of the first measuring means, the status of the patient can be controlled more reliably, while harming and/or disturbing the patient with measurements whose results are of less use can be avoided in most applications.

The type of patient can be determined in home situations and under ambulant conditions.

The daily amount of a drug to be administered outside the effective window may be lowered, thus limiting side effects of the drug.

The release of the drug can be personalized/individualized according to the patient's needs based on the patient's own rhythm.

The term "measuring cycle" means and/or includes especially that a body parameter of the patient is measured which is known to behave in a cyclic and/or periodic manner, e.g. the body temperature. A measuring cycle in the sense of the present invention may last a day (circadian), however, also longer (e.g. infradian) and/or shorter cycles (ultradian) are feasible and also embodiments of the present invention. According to an embodiment of the present invention, no drug is dispensed by the device during the measuring cycle.

The term "normalized curve" means and/or includes especially that the data derived from the measuring cycles is used to calculate the normalizing curve by means of the equation:

$$Z = (X - \text{mean}(X))/\text{standard deviation} * 100\%$$

with X (also written as $X_t$) being the body parameter and mean(X) being the mathematical average of $X_t$ over a defined period. It should be noticed that usually X may have both positive and negative values.

However, in case the first body parameter includes activity, for a wide range of applications within the present invention the normalizing curve is calculated by:

Taking the average diurnal activity, taking the actual average (measured at intervals of 10 to 30 minutes) activity and dividing the actual average activity by the average diurnal activity.

The data used in this application is presented in % on a normalized scale; however it goes without saying that this is merely for the sake of a better understanding and any person skilled in the art may easily transform the data to any given scale known in the field.

The term "monitoring cycle" means and/or includes especially that during this cycle the second measuring means is started (possibly after a certain delay). A monitoring cycle in the sense of the present invention may last a day (circadian), however, also longer (e.g. infradian) and/or shorter cycles (ultradian) are feasible and also embodiments of the present invention.

It goes without saying that the data obtained in this monitoring cycle may be used for normalization of the curve as well, so that in an embodiment of the present invention some of the monitoring cycles are measuring cycles and vice versa.

According to an embodiment of the present invention, the at least one first body parameter includes body temperature, core body temperature, skin surface temperature, activity (body or brain), heart rate, melatonin level, triacylglycerol level, cortisol level.

According to an embodiment of the present invention, the at least one second body parameter includes blood pressure.

It should be noted that "blood pressure" means and/or includes diastolic as well as systolic blood pressure, and either one or both may be measured.

According to an embodiment of the present invention, the second measuring means starts measuring when during the at least 1 monitoring cycle a change in the normalized monitoring data is observed of ≥40%/hour (on the normalized scale) over ≥1 hours.

According to an embodiment of the present invention, the second measuring means starts measuring when during the at least 1 monitoring cycle a change in the normalized monitoring data is observed of ≥60%/hour (on the normalized scale) over ≥1 hours.

It should be noted that a "change" (of one or more monitored parameters of a first measuring means) according to the present invention includes especially a rise and/or a decline in the normalized curve. Depending on the actual indication, the measurement of the second body parameter may start when only a rise is detected or only a decline, or on both occasions.

According to an embodiment of the present invention, in case that several body parameters are measured by the measuring means of the first body parameter, the measuring means for the second body parameter may be started when all body parameters show a change as described above. However, according to an embodiment of the present invention, the measuring means for the second body parameter is started when only one (or more) of the first body parameters, but not necessary all, show the change as described above.

According to an embodiment of the present invention, the second measuring means starts measuring when during the at least 1 monitoring cycle a drop in the normalized monitoring data is observed of ≥40%/hour (on the normalized scale) over ≥1 hours.

According to an embodiment of the present invention, the second measuring means starts measuring when during the at least 1 monitoring cycle a drop in the normalized monitoring data is observed of ≥40%/hour (on the normalized scale) over ≥1 hours and/or the normalized data falls under (the absolute value of) 50%.

It should be noted that for a wide range of applications within the present invention, this embodiment is used when the first body parameter includes body temperature, core body temperature, skin surface temperature, activity (body or brain).

According to an embodiment of the present invention, the second measuring means starts measuring when during the at least 1 monitoring cycle a drop in the normalized monitoring data is observed of ≥40%/hour (on the normalized scale) over ≥1 hours and/or the normalized data falls under (the absolute value of) 40%.

It should be noted that for a wide range of applications within the present invention, this embodiment is used when the first body parameter includes body temperature, core body temperature, skin surface temperature.

According to an embodiment of the present invention, the second measuring means starts with a pre-selected delay in the range of ≥0.5 and ≤3 hours when during the at least 1 monitoring cycle the first normalized monitoring data deviates from the maximum point of the first normalized curve by a threshold value of ≤5%.

It should be noted that for a wide range of applications within the present invention, this embodiment is used when the first body parameter includes body temperature, core body temperature, skin surface temperature.

According to an embodiment of the present invention, the second measuring means is stopped within 1 hour when during the at least 1 monitoring cycle the normalized monitoring data deviates from the normalized 0%-point of the normalized curve by a threshold value of ≤5% and is increasing.

According to an embodiment of the present invention, the second measuring means is stopped immediately when during the at least 1 monitoring cycle the normalized monitoring data deviates from the normalized 0%-point of the normalized curve by a threshold value of ≤5% and is increasing.

It should be noted that for a wide range of applications within the present invention, this embodiment is used when the first body parameter includes body temperature, core body temperature, skin surface temperature.

According to an embodiment of the present invention, the second measuring means is stopped when during the at least 1 monitoring cycle an average increase in the normalized monitoring data is observed of ≥25%/hour (on the normalized scale) over ≥5 hours.

It should be noted that for a wide range of applications within the present invention, this embodiment is used when the first body parameter includes body temperature, core body temperature, skin surface temperature.

According to an embodiment of the present invention, the second measuring means is stopped when during the at least 1 monitoring cycle an average increase in the normalized monitoring data is observed of ≥40%/hour (on the normalized scale) over ≥1 hours and the normalized data rises above (the absolute value of) 40%.

According to an embodiment of the present invention, the second measuring means is stopped when during the at least 1 monitoring cycle an average increase in the normalized monitoring data is observed of ≥40%/hour (on the normalized scale) over ≥1 hours and the normalized data rises above (the absolute value of) 50%

It should be noted that for a wide range of applications within the present invention, this embodiment is used when the first body parameter includes body temperature, core body temperature, skin surface temperature.

According to an embodiment of the present invention, the device furthermore comprises a fitting means which generates a fitting curve of the data of the second body parameter.

According to an embodiment of the present invention, in case the second body parameter includes blood pressure, the fitting means fits the second body parameter data to the following fitting curve $$[curve] = Mesor + A1*\cos(2\pi*(time - Acrophase1)/Period1) + A2*\cos(2\pi*(time - Acrophase2)/Period2)$$

where preferably period2 is a fraction of period1.

According to an embodiment of the present invention, the device comprises a drug delivery device which is chosen from transdermal patches, epills, implants, especially drug delivery and/or drug releasing implants.

It should be noted that according to an embodiment of the present invention, the measuring and normalizing means are included in the drug delivery device, whereas according to another embodiment of the present invention, they are separate. In the latter case, according to an embodiment of the present invention, the data and/or a start signal are transferred to the drug delivery device in order to start the drug release program when needed.

The present invention also relates to a method for the controlled release of drugs and/or monitoring the status of a patient, comprising the steps of a) measuring at least one body parameter of the patient for at least 1 measuring cycle and at least 1 monitoring cycle, b) generating a normalized curve for each of the measured body parameter(s) of the patient from the data obtained in the measuring cycles and adjusting the data obtained in the at least one monitoring cycle to normalized data based on the normalized curve to obtain normalized monitoring data, c) starting and/or stopping the measurement of at least one second body parameter in response to the output of the normalizing means of the at least one first body parameter, d) optionally, generating a fitting curve of the data of the at least one second body parameter, e) optionally, starting a drug release based upon the comparison of the data of step c) and/or d) with a comparison means.

According to an embodiment of the present invention, the drug release program includes a delay of ≥0 and ≤24 hours prior to the release of drugs.

According to an embodiment of the present invention, the drug release program includes a delay of ≥0 and ≤7 measuring cycles prior to the release of drugs.

The invention furthermore relates to the use of a device for drug administration and/or monitoring the status of a patient of the invention for the diagnosis and/or treatment of hypertension and/or normotension.

Especially in hypertension it has been shown that chronobiological aspects may play an important role. Without being fixed to a certain theory, the following is believed to play an aspect in the diagnosis and/or treatment of hypertension and/or normotension:

Hypertensive and normotensive patients tend to display the same circadian pattern, exhibiting a peak in blood pressure during the morning hours and a trough at night during sleep. There is often a rapid increase in blood pressure beginning at approximately 6 AM, just prior to awakening. This morning surge in blood pressure often continues for 4 to 6 hours after awakening and is characterized by an increase in systolic blood pressure (SBP) of approximately 3 mm Hg per hour, and in diastolic blood pressure (DBP) of approximately 2 mm Hg per hour. After the morning surge in blood pressure, levels begin to decline. Between about 8 PM and 2 AM, readings fall 15 to 20 mm Hg to reach their lowest point several hours after midnight. As a result of these fluctuations, daytime blood pressure typically is 10% to 20% higher than nighttime blood pressure, with the highest readings recorded during the morning surge from 6 AM until noon.

It has been shown for a wide range of applications that a device according to the present invention may take greater account of these circadian patterns and therefore may be of use for the diagnosis and/or treatment of hypertension and/or normotension.

A device according to the present invention may be of use in a broad variety of systems and/or applications, amongst them one or more of the following:

medical devices for the administration of drugs
medical devices for treatment of chronic diseases The aforementioned components, as well as the claimed components and the components to be used in accordance with the invention in the described embodiments, are not subject to any special exceptions with respect to their size, shape, material selection and technical concept, so that the selection criteria known in the pertinent field can be applied without limitations.

BRIEF DESCRIPTION OF THE DRAWINGS

Additional details, features, characteristics and advantages of the object of the invention are disclosed in the subclaims, the Figures and the following description of the respective Figures, tables and examples.

The invention will furthermore be better understood by means of the following examples of some applications in which a device according to the present invention may be used, but which are merely to be understood as exemplarily and not limiting the scope of the present invention.

Figure 1:
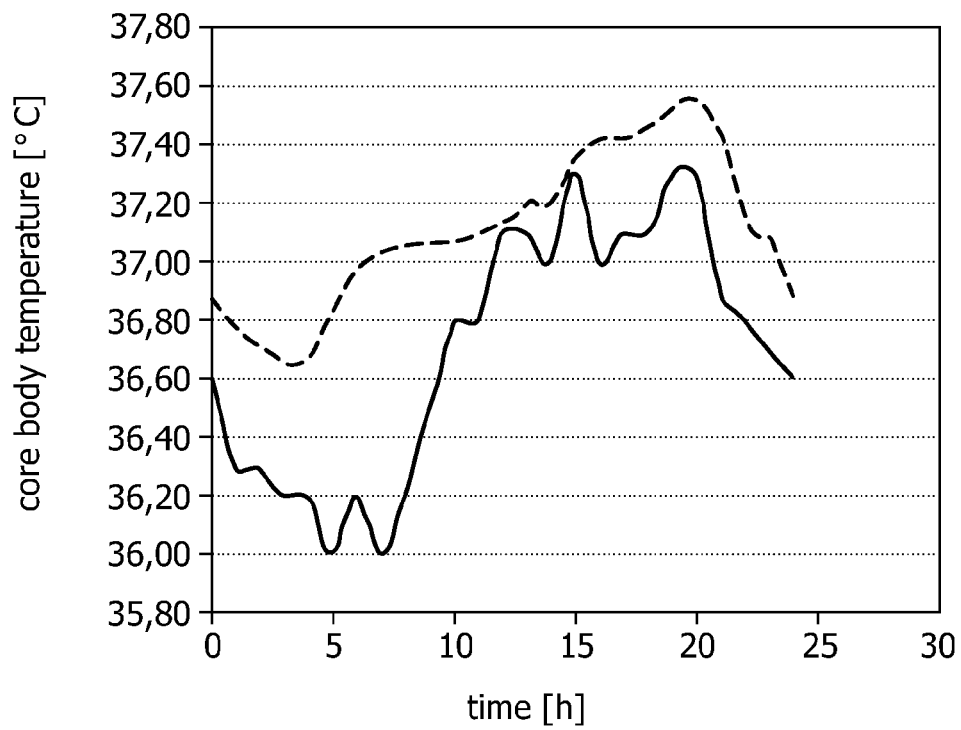
FIG. 1 shows a diagram of measurements of a first body parameter of a patient.
Figure 2:
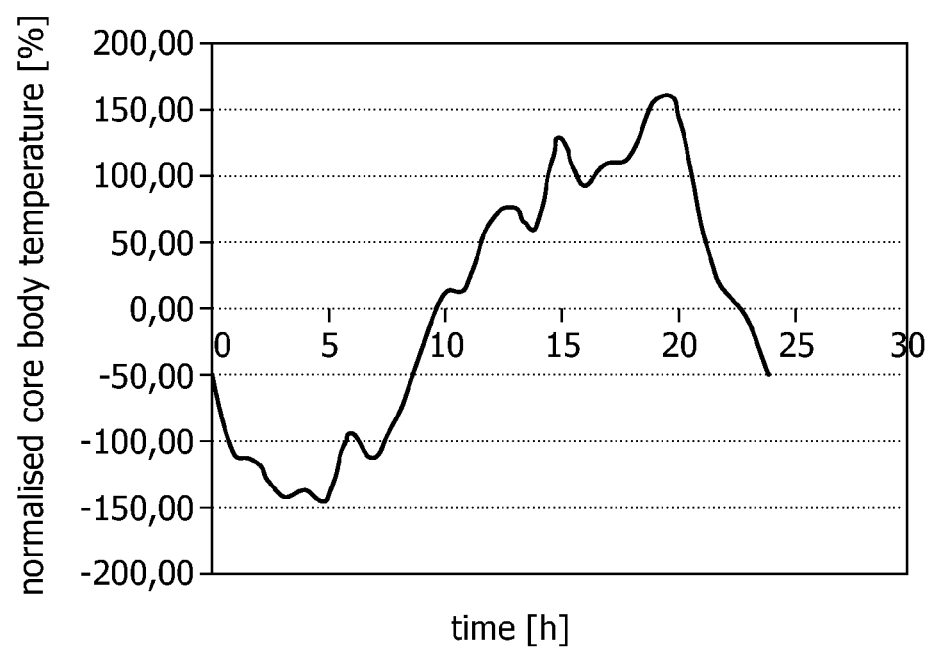
FIG. 2 shows a diagram of the normalized data of the data from FIG. 1.

FIGS. 1 and 2 refer to the measurement of a first body parameter of a patient, which in this example is body temperature. The exact data are shown in Table I:

TABLE I

| time [h] | ° C. day 1 | ° C. day 2 | Averaged temperature | Normalized data |
|---|---|---|---|---|
| 0 | 36.60 | 36.87 | 36.74 | −49.72 |
| 1 | 36.30 | 36.78 | 36.54 | −108.33 |
| 2 | 36.30 | 36.72 | 36.51 | −117.35 |
| 3 | 36.20 | 36.65 | 36.43 | −142.90 |
| 4 | 36.20 | 36.68 | 36.44 | −138.39 |
| 5 | 36.00 | 36.84 | 36.42 | −144.40 |
| 6 | 36.20 | 36.97 | 36.59 | −94.80 |
| 7 | 36.00 | 37.04 | 36.52 | −114.34 |
| 8 | 36.20 | 37.06 | 36.63 | −81.28 |
| 9 | 36.50 | 37.07 | 36.79 | −34.69 |
| 10 | 36.80 | 37.07 | 36.94 | 10.40 |
| 11 | 36.80 | 37.10 | 36.95 | 14.91 |
| 12 | 37.10 | 37.13 | 37.12 | 64.50 |
| 13 | 37.10 | 37.21 | 37.16 | 76.53 |
| 14 | 37.00 | 37.20 | 37.10 | 60.00 |
| 15 | 37.30 | 37.36 | 37.33 | 129.13 |
| 16 | 37.00 | 37.42 | 37.21 | 93.06 |
| 17 | 37.10 | 37.42 | 37.26 | 108.09 |
| 18 | 37.10 | 37.46 | 37.28 | 114.10 |
| 19 | 37.30 | 37.53 | 37.42 | 154.68 |
| 20 | 37.30 | 37.55 | 37.43 | 157.68 |
| 21 | 36.90 | 37.42 | 37.16 | 78.03 |
| 22 | 36.80 | 37.13 | 36.97 | 19.42 |
| 23 | 36.70 | 37.07 | 36.89 | −4.63 |
| 24 | 36.60 | 36.87 | 36.74 | −49.72 |

FIG. 1 shows the data for day 1 (continuous line) and day 2 (dotted line). Out of this measurement a normalized curve was generated which is shown in FIG. 2.

Using this data, a second body parameter (in this example, blood pressure) was measured, too. In this particular example, the second measuring means was set to measure when during the at least 1 monitoring cycle a drop in the normalized monitoring data was observed of ≥40%/hour (on the normalized scale) over ≥1 hours. The second measuring means started with a pre-selected delay of at least 1 hour.

In this particular example, the second measuring means was set to stop immediately when during the at least 1 monitoring cycle the normalized monitoring data deviated from the normalized 0%-point of the normalized curve by a threshold value of ≤5% and was increasing.

From the normalized data it can be seen that the time for measuring is between 0:00 and 10:00 hrs and between 22:00 and 24:00 hrs. However, for demonstrating the accuracy of the fit, it was continuously measured and the data in between this time was also used. The data is given in table II:

TABLE II

| time [h] | BP [mm Hg] |
|---|---|
| 0 | 118.2 |
| 2 | 110.6 |
| 4 | 110.6 |
| 6 | 118.6 |
| 8 | 132.2 |
| 10 | 136.6 |
| 12 | 131.4 |
| 14 | 126.2 |
| 16 | 124.6 |
| 18 | 128.2 |
| 20 | 133.0 |

TABLE II-continued

| time [h] | BP [mm Hg] |
|---|---|
| 22 | 127.4 |
| 24 | 118.2 |

Figure 3:
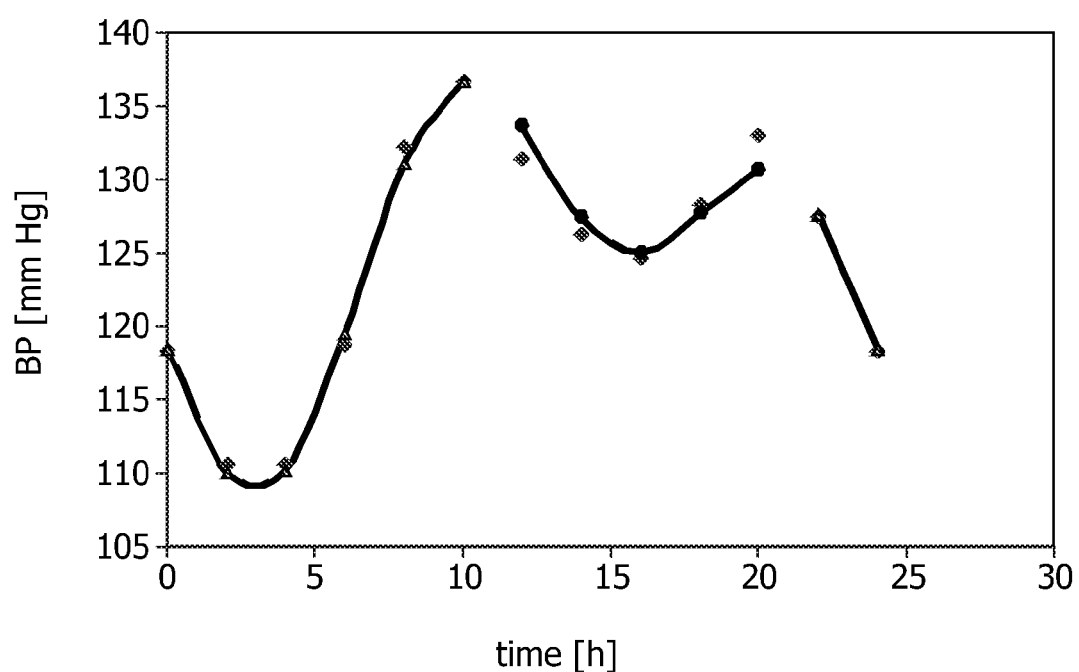
FIG. 3 shows a diagram of a measurement of a second body parameter of the same patient and fitting curves to that measurement.

FIG. 3 shows a diagram of the data of Table II, where only the time from 0:00 and 10:00 hrs and from 22:00 to 24:00 was used for the fitting. The fitting curve corresponds to the equation

[curve]=Mesor+$A1$*cos($2\pi$*(time−Acrophase1)/Period1)+$A2$$2\pi$*cos($2\pi$*(time−Acrophase2)/Period2)

with

Mesor=124.8 mm Hg, $A1$=8.7 mm Hg, acrophase1=13.9 h, period1=24 h, $A2$=7.8 mm Hg, acrophase2=9.3h, period2=12h, (time: 0-24 h)

and is shown in FIG. 3 for the blood pressure as a function of time which was used for the fitting ("triangles") as well as for the blood pressure calculated as a function of time at which no actual BP measurement was performed "between the stated times" ("circles").

It can be seen that although only a part of the data was used, the fitting is quite good throughout the day. This shows that it is possible for most applications to partially skip the measurement of the second body parameter without affecting the quality of the (daily) data.

The particular combinations of elements and features in the above detailed embodiments are exemplary only; the interchanging and substitution of these teachings with other teachings in this application and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. A method for the controlled release of drugs and/or monitoring the status of a patient, the method comprising:
    a) measuring at least one body parameter of the patient for at least three measuring cycles and at least one monitoring cycle,
    b) generating a normalized curve for each of the measured body parameter(s) of the patient from the data obtained in the measuring cycles and adjusting the data obtained in the at least one monitoring cycle to normalized data based on the normalized curve to obtain normalized monitoring data,
    c) starting and/or stopping a measurement of at least one second body parameter having a circadian variation in response to observed deviations of the normalized data on a normalized scale or observed deviations of the normalized monitoring data,
    d) generating a fitting curve of data of the at least one second body parameter, and
    e) starting a drug release by a drug release device based upon comparison of the data of step c) and/or d).

2. The method according to claim 1, wherein the at least one first body parameter includes body temperature, core body temperature, skin surface temperature, body activity, brain activity, heart rate, melatonin level, triacylglycerol level, cortisol level.

3. The method according to claim 1, wherein the at least one second body parameter is blood pressure.

4. The method according to claim 1, wherein the second measuring means starts measuring when during the at least 1 monitoring cycle a change in the normalized monitoring data is observed of ≥40%/hour on a normalized scale over ≥1 hours.

5. The method according to claim 1, wherein the second measuring means starts measuring when during the at least 1 monitoring cycle a drop in the normalized monitoring data is observed of ≥40%/hour on a normalized scale over ≥1 hours and/or the normalized data falls under an absolute value of 50%.

6. The method according to claim 1, wherein the second measuring means is stopped when during the at least 1 monitoring cycle the normalized monitoring data deviates from the normalized 0%-point of the normalized curve by a threshold value of ≥5% and is increasing.

7. The method according to claim 1, wherein the second measuring means is stopped when during the at least 1 monitoring cycle an average increase in the normalized monitoring data is observed of ≥40% hour on a normalized scale over hours and/or the normalized data rises above an absolute value of 40%.

8. The method according to claim 1, wherein the comparison of the data of step c) and/or d) comprises the comparison of the data of step c) and/or d) with pre-stored comparison data.

* * * * *